United States Patent [19]

Heusser

[11] Patent Number: 4,845,983

[45] Date of Patent: Jul. 11, 1989

[54] TESTING APPARATUS FOR TEXTILE STRANDS

[75] Inventor: Eduard Heusser, Uster, Switzerland

[73] Assignee: Zellweger Uster AG, Uster, Switzerland

[21] Appl. No.: 116,783

[22] Filed: Nov. 5, 1987

[30] Foreign Application Priority Data

Nov. 6, 1986 [CH] Switzerland .......................... 4432/86
Nov. 6, 1986 [CH] Switzerland .......................... 4433/86

[51] Int. Cl.$^4$ ............................................. G01N 27/24
[52] U.S. Cl. ........................................ 73/160; 242/36;
324/61 R
[58] Field of Search ............... 73/159, 160; 324/60 C,
324/61 R; 361/278; 28/227, 232, 233, 234, 235;
242/36; 224/61 P

[56] References Cited

U.S. PATENT DOCUMENTS

| | | | |
|---|---|---|---|
| 2,950,436 | 8/1960 | Butticaz et al. | 361/280 |
| 3,754,172 | 8/1973 | Hoffmann | 361/278 |
| 3,788,138 | 1/1974 | Heusser | 73/160 |
| 3,805,607 | 4/1974 | Heusser | 73/160 |
| 3,960,593 | 6/1976 | Heusser | 73/160 |
| 4,706,014 | 11/1987 | Fabbri | 73/160 |

Primary Examiner—William M. Shoop, Jr.
Assistant Examiner—Brian K. Young
Attorney, Agent, or Firm—Burns, Doane, Swecker & Mathis

[57] ABSTRACT

The apparatus contains a measuring comb for the material to be tested. The plate like projections of the comb define measuring gaps of different widths through which the material passes to be tested for determining characteristic magnitudes associated with that material. The measuring comb is adjustable transversely to the direction of movement of the test sample and each measuring gap is adjustable to a nominal position. Consequently, the test sample passes through each measuring gap under the same geometrical conditions and is not subjected to deflections which vary from one measuring gap to another. A device for temporarily removing the test sample from the measuring gap, and subsequently guiding it back into the gap, is arranged in the region of the measuring comb so that the zero setting of the apparatus may be adjusted. This not only relieves the operator of the task of manually removing the test material from the measuring gap but also ensures that the test material will subsequently be returned to the correct measuring gap.

20 Claims, 4 Drawing Sheets

TESTING APPARATUS FOR TEXTILE STRANDS

FIELD OF THE INVENTION

This invention relates to an apparatus for the automatic determination of characteristic magnitudes of textile material to be tested, such a yarns, rovings and slivers. Such an apparatus often is referred to as a "tester". In a well known type of tester, characteristics of a textile strand are sensed as the strand is moved lengthwise through a measuring gap. The present invention is concerned particularly with features which relate to the positional relationship between strand and measuring gap.

BACKGROUND

In textile laboratories, especially of spinning mills, spot checks are carried out on random samples by way of quality control to determine certain textile parameters such as fluctuations in weight and other characteristic quantities which can be derived from these measurements. These tests are carried out by means of so called uniformity testers of the kind, for example, which are distributed world wide by Zellweger Uster AG under the registered trademark USTER.

Typically a uniformity tester includes a measuring unit containing a guide device, a measuring instrument, a feed device and a draw-off device for the sample to be tested. The measuring instrument itself is formed by a measuring comb with plate-like projections defining gaps of different widths between them through which the sample may be passed to determine the characteristic magnitudes. Each measuring gap is the air gap of a capacitor, and the aforesaid magnitudes for the sample are measured capacitively.

In the known uniformity testers, the samples pass through the measuring unit while being stretched between other components, e.g. between the guide device and the draw off device. The sample is inserted into the measuring gap whose width is suitable for the particular sample, and this procedure generally causes it to be deflected from its normal position between the guide device and the draw off device.

In attempts to provide further improvement to this known uniformity tester with a view to obtaining very exact and representative measurement results, it has been found that one important factor is to ensure that the material being tested will always take up the same position, as far as possible, in the measuring unit. Every deflection of the material from its normal position results in undesirable deviation.

Also to be considered are the operational aspects of inserting the sample into a particular measuring gap and removing it therefrom. To determine the fluctuations in weight of the sample to be tested, the sample is pulled through one of the gaps of the measuring comb by the feed device, the choice of measuring gap being determined by the fineness or yarn count of the material. An insertion mechanism for the sample to be tested is associated with the measuring unit. This mechanism grips the material and inserts it into the predetermined measuring gap.

Since it is necessary to adjust the measuring unit to zero or check the zero setting at least at the beginning of each measurement, the test sample already inserted in its measuring gap must be briefly removed from the gap. This had hitherto to be carried out manually by the operator.

However, removal of the test sample from the measuring gap by hand for adjusting the apparatus to zero not only constitutes a source of error but also is not operator friendly.

OBJECTS AND SUMMARY OF THE INVENTION

An object of the present invention is to improve the known uniformity testers so that the sample being tested will always assume the same specified position in the measuring unit, regardless of which measuring gap is used.

Another object of the invention is to provide a uniformity tester of increased reliability and ease of use by including in the tester means for removing the test sample from the measuring gap which not only relieves the operator but also avoids possible operational errors since the material is automatically returned to the correct measuring gap.

In apparatus according to this invention, the required measuring gap of the measuring comb is always automatically adjusted to the nominal position of the sample as defined by its stretched position between the guide device and the draw off device so that the sample will not suffer any deflection from its normal position even when it is changed to a different measuring gap. The measuring comb is mounted for adjusting movements in a direction at right angles to the direction of travel of the strand being tested, and such movements of the measuring comb are controlled by means which cause the comb to be stopped each time at the correct position to assure proper coaction between the strand and the selected measuring gap.

For dealing with the task of moving the strand out of its normal path relative to the measuring comb at times between test sequences, there is provided in accordance with the invention a lifter system in which a strand contacting element near the measuring comb is moved a predetermined distance to displace the strand path sufficiently to clear the measuring gaps completely. After the measuring unit has been adjusted to zero, the apparatus is actuated to return the strand contacting element to an original position behind the nominal strand path through the measuring comb and allow the strand to enter the selected measuring gap.

BRIEF DESCRIPTION OF THE DRAWINGS

The invention will now be described with reference to the accompanying drawings, in which.

DETAILED DESCRIPTION OF PREFERRED EMBODIMENTS

Figure 1:
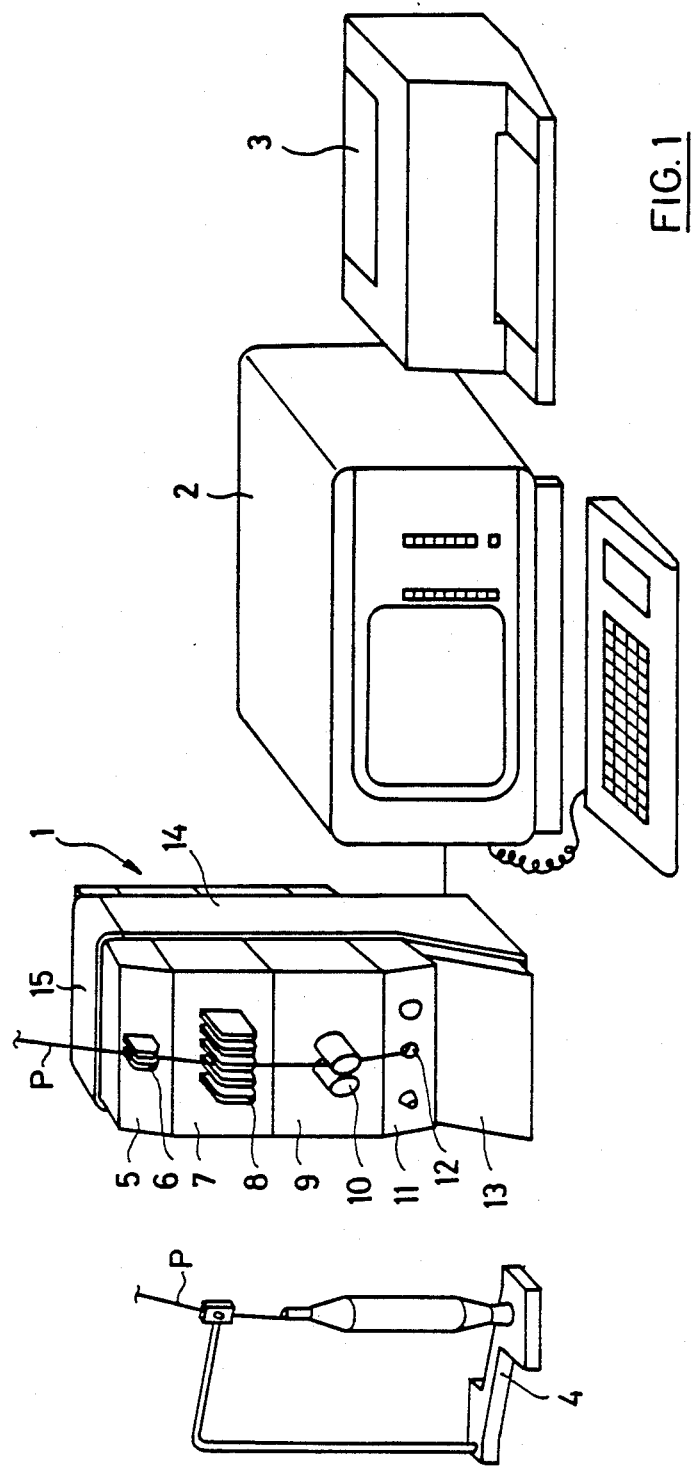
FIG. 1 is a view in perspective of a uniformity tester for determining the fluctuations in weight of staple fibre yarn.

The uniformity tester illustrated in FIG. 1 for determining fluctuations in weight of textile material to be tested, such as yarns, rovings or slivers of staple fibers, comprises, as illustrated, a measuring unit 1, an interpreting unit 2, an output element 3 and a framework 4 for the packages of test material P, such as spools of yarns or rovings. Uniformity testers of this type are known and are distributed worldwide by Zellweger Uster AG under the trademark USTER.

The measuring unit 1 for the test material P consists, as illustrated, of several modules which are arranged in the following order in the direction of travel of the test sample P, i.e. from above downwards in the drawing: first, a module 5 provided with a thread guiding device 6, for example a thread brake; then module 7 equipped with a measuring instrument 8; followed by a module 9 carrying a feed device 10; and finally a module 11 with a draw off suction nozzle 12. The lowermost module 11 is mounted on a base 13 and all the aforesaid modules 5, 7, 9 and 11 together with the base 13 are fitted into a frame 14 having a stirrup-shaped upper part 15 and are held by this frame.

The measuring instrument 8 through which the test sample P is drawn by the feed device 10, which consists of a pair of rollers, is a so called capacitive measuring instrument. This has been described in U.S. Pat. Nos. 3,754,172; 3,788,138; and 3,805,607; the disclosures of which are incorporated herein by reference. The draw off suction nozzle 12 is already known from the above mentioned USTER tester and need not be described here.

The interpreting unit 2 contains inter alia an analog-to-digital converter and a computer and is combined with a display screen, as shown. The electric signals continuously produced by the measuring instrument 8 are processed by the computer of the interpreting unit 2 and stored in some suitable form in a memory integrated with the interpreting unit 2 and may be displayed on the screen before being printed out on the output unit 3. This has the advantage that all data obtained may first be displayed on the screen and only selected data need be printed out by the printer 3.

It should be noted that the signal processing device in the interpreting unit 2 has three main components, namely a spectrograph for the so called spectrogram (wave length spectrum of fluctuations in weight), an imperfection indicator, which counts the excesses of weight above the limiting value, and an interpreting part proper for determining the so called variation coefficients and the length variation graph. All these parameters are already known from the USTER tester.

If the uniformity tester is required to determine fluctuations in weight of filament yarns, the measuring unit 1 should differ from that shown in the drawing in several respects. A different measuring instrument particularly appropriate for filament yarns is required, although this is again a capacitive measuring instrument. Instead of locating te feed device 10 downstream of the measuring instrument 8, it should be arranged upstream of the measuring instrument 8 when filament yarns are to be tested. Also, a special draw off suction nozzle is required to impart to the filament yarn the twist required for the test. For details of this type of suction nozzle, see U.S. Pat. No. 3,951,321, the disclosure of which is incorporated herein by reference.

The measuring unit 1 may be provided with additional modules so that it may also be used for determining other parameters of the test material P. Thus, for example, an additional module equipped with an instrument for measuring the hairiness of the test material P may be inserted so that both the hairiness and the fluctuations in weight of the sample P may be determined in a single passage through the measuring unit 1. For such a measuring unit, see Swiss Patent Application No. 02 823/86-2 in the name of the assignee of the present patent application.

As the test sample P passes through the measuring unit 1 in the course of the tests, it is stretched between the thread guide device 6 and the suction nozzle 12, and the two rollers which form the feed device 10 are so arranged that they will not deflect the sample P from its straight path.

Figure 2:
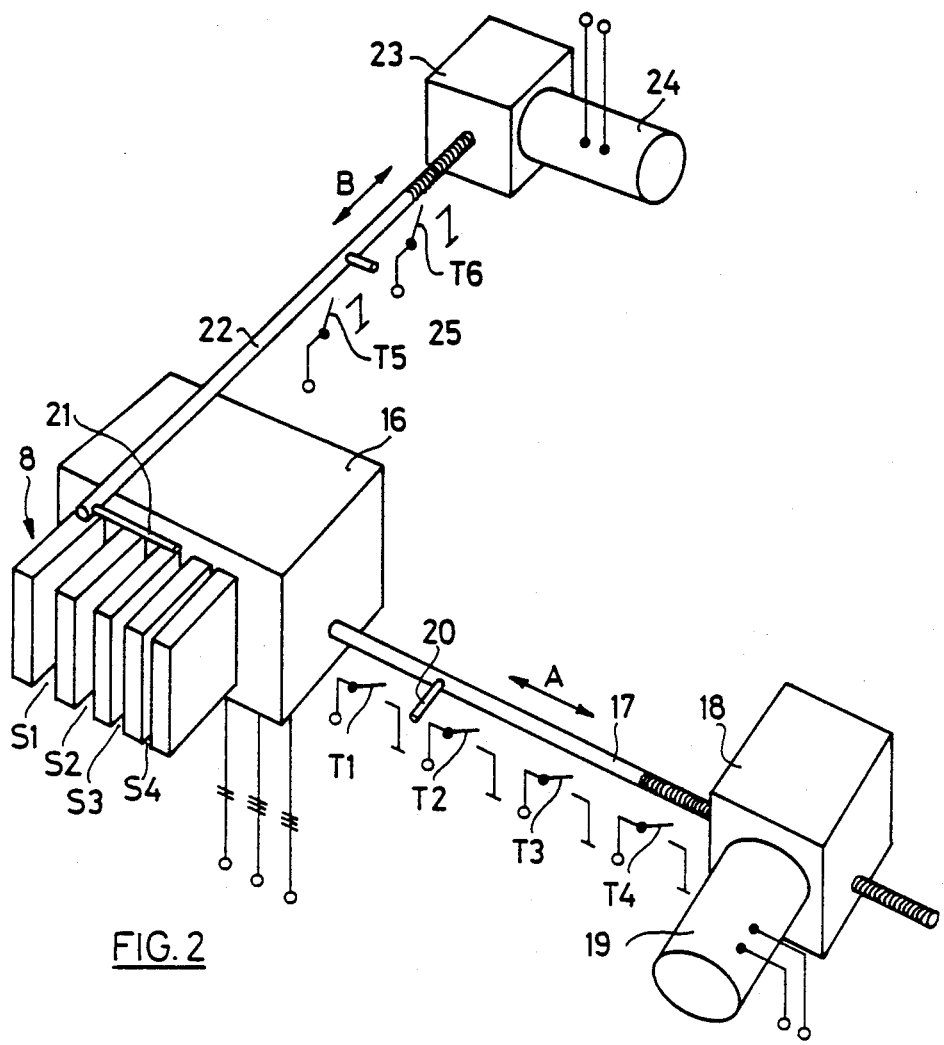
FIG. 2 is a view in perspective of the essential parts of the measuring instrument of the measuring unit of the uniformity tester.

FIG. 2 is a view in perspective of the main parts of the measuring instrument 8 of the measuring unit 1 of the uniformity tester of FIG. 1. As already mentioned, the measuring instrument is a so called capacitive measuring instrument and consists of a detector component (sometimes referred to herein as a "measuring comb" with plate like projections which define measuring gaps S1, S2, S3, S4 of different widths. The sample under test is passed through a particular measuring gap S1, S2, S3 or S4, depending on its yarn count.

In order to ensure that the test sample will not be deflected from its normal path when it is inserted in the various measuring gaps S1 to S4, the measuring comb 8 is designed to be displaceable transversely to the direction of movement of the sample, and the axis of each measuring gap S1 to S4 can be adjusted to a specified nominal position. It is important that this nominal position should always be the same so that the test sample will either not be deflected at all (nominal position specified by the normal position of the stretched sample) or at least will always be deflected by the same amount.

To enable the measuring comb 8 to be thus displaceable and adjustable, it is mounted on a supporting block 16 which also carries a threaded rod or spindle 17 extending in the direction of displacement of the measuring comb 8. The threaded portion of this spindle 17 is mounted in a driving unit 18 which is fixed in the module 7 (FIG. 1) and comprises a motor 19 and a means (not shown) driven by this motor and engaging the threaded portion of rod 17, so that when such means is rotated by the motor 19 the rod 17 will be moved axially. The means for engaging the threaded portion of the rod 17 may be an internally threaded nut which threadedly cooperates with the rod and which is itself rotated by the motor 19 and fixed against bodily mooement in the direction of the axis of the rod 17. When the motor 19 is switched on to rotate in one or other direction, the threaded nut means is rotated in the same direction and the threaded spindle 17 is moved to the left or the right in the direction of the double arrow A together with the supporting block 16 and the measuring comb 8. Each of the measuring gaps S1 to S4 is associated with one of the switches T1 to T4 arranged along the threaded spindle 17, these switches being operated by an element 20 projecting laterally from the spindle 17.

To put the uniformity tester into operation, the operator feeds the required measuring gap S1, S2, S3 or S4 into the interpreting unit 2 (FIG. 1) and thereby starts the motor 19 which displaces the threaded spindle 17 in the direction of the arrow A until the element 20 makes contact with the appropriate switch T1, T2, T3 or T4 corresponding to the required measuring gap. Since with each test the yarn count is also fed into the interpreting unit 2 and there is a unique relationship between the yarn count and the required measuring gap, the gap may also be selected automatically on the basis of the yarn count fed into the interpreting unit.

Before each test is carried out, the sample is placed into the appropriate measuring gap Sl, S2, S3 or S4 by means of an inserting mechanism (not shown). The measuring unit 1 (FIG. 1) must then be set at zero or the zero setting must be checked.

A stirrup shaped yarn lifter 21 sometimes referred to herein as a "finger" situated above the measuring comb 8 and extending in the direction of the depth of the measuring gaps is provided for this purpose. This yarn lifter or finger 21 is mounted on a threaded rod or spindle 22 which is displaceable in the above mentioned direction. This threaded rod or spindle 22 is mounted in a fixed driving unit 23 which has a motor 24 and means (not shown) for coupling the rod 22 to the motor in the way that the spindle 17 is coupled to motor 19. When the motor 24 is switched on, the threaded spindle 22 is moved forwards or backwards in the direction of the double arrow B and the test sample lying on the yarn lifter 21 is thereby either moved out of its measuring gap or is enabled to slide into the gap.

The spindle 22 has a laterally projecting element 25, and two switches T5 and T6 arranged in the path of this element 25 stop the motor 24 when actuated by the element 25. Starting the motor 24 and thereby moving the test sample out of the measuring gap for the purpose of setting the apparatus to zero is always carried out either between two tests or at the end of a test series.

Figure 3:
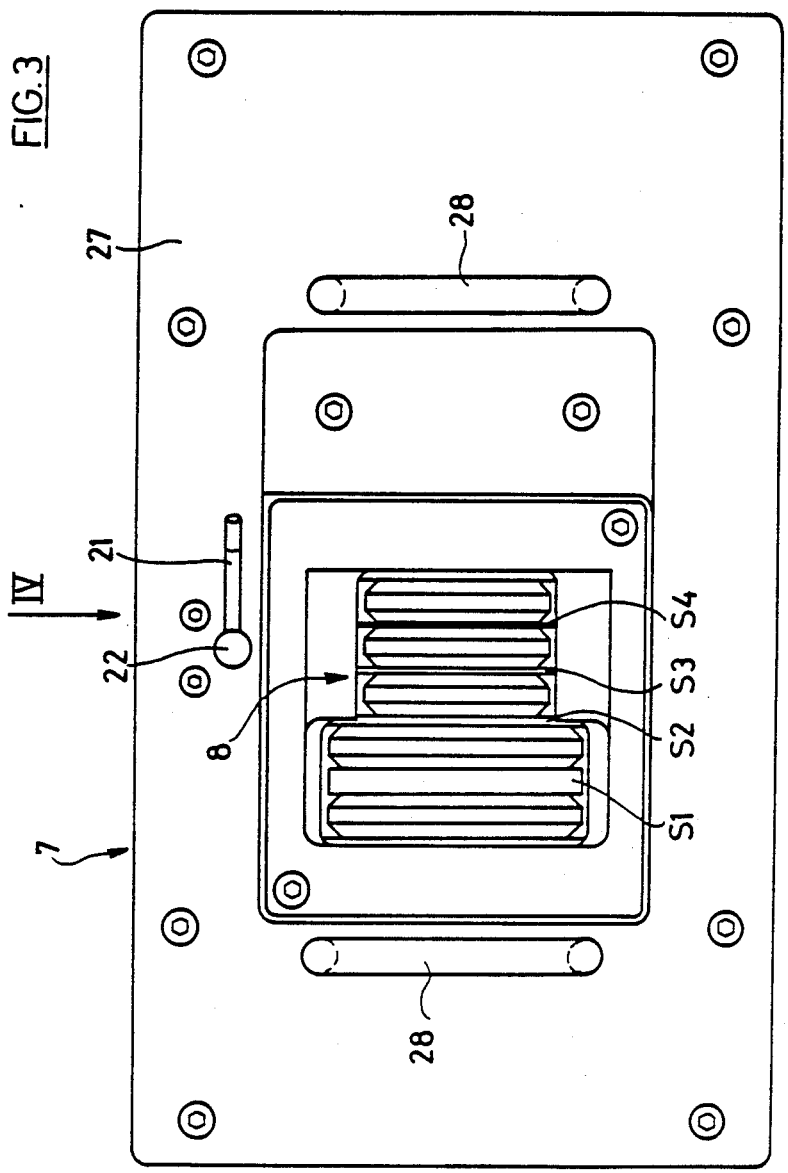
FIG. 3 is a front view of part of the measuring unit.
Figure 4:
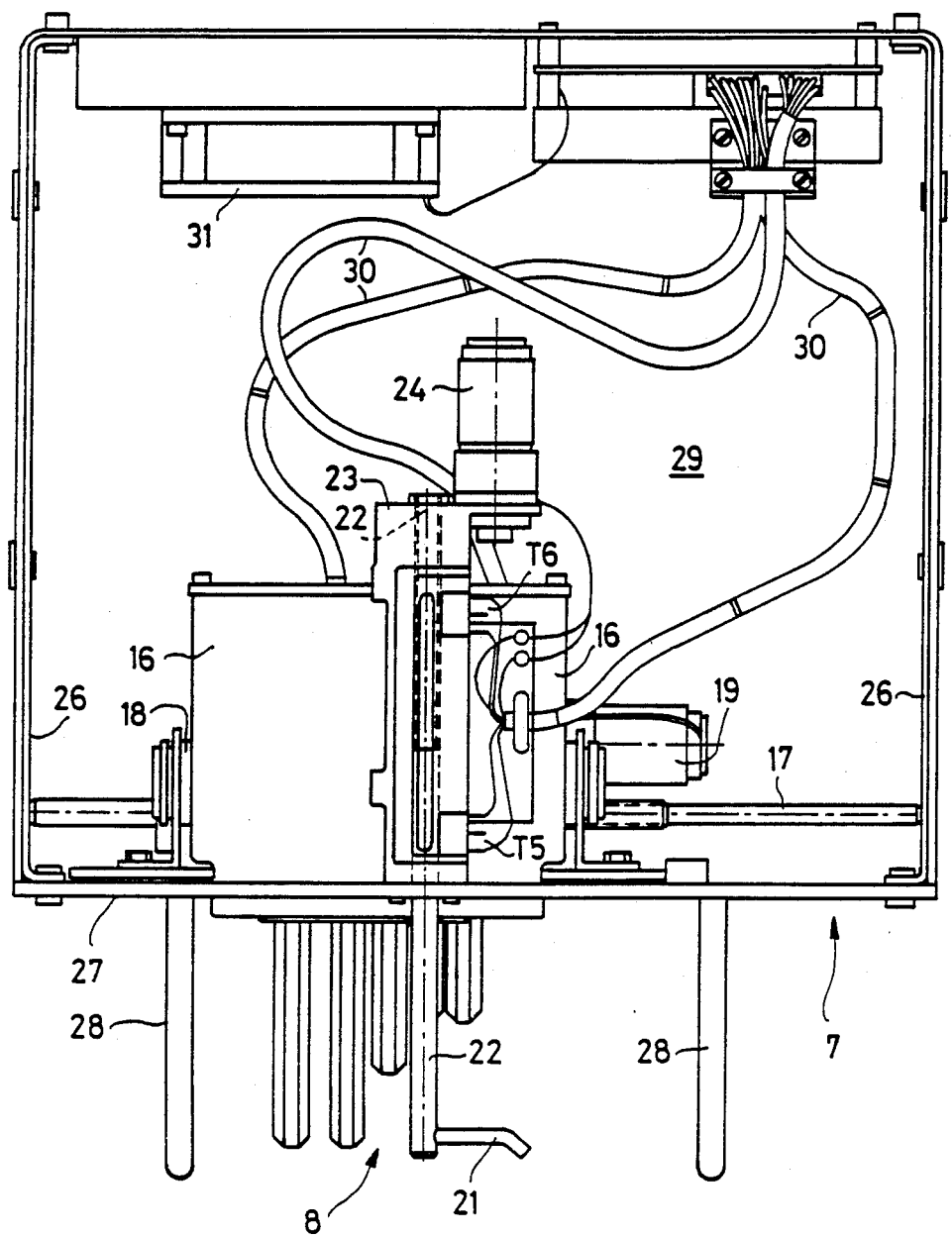
FIG. 4 is an elevational view in the direction of the arrow IV of FIG. 3 with the housing plate removed.

FIGS. 3 and 4 show the actual arrangement of the parts shown in FIG. 2 in the module 7 (FIG. 1). The module 7 consists, as shown, of a more or less prismatic housing 26 which is pushed into the frame 14 (FIG. 1). The measuring comb 8 with its measuring gaps Sl to S4 of four different widths, which are four in number in the drawing, and the yarn lifter 21, project from the front plate 27 of the housing 26. On each side of the measuring comb 8, a stirrup shaped handle 28 projects from the front plate 27 for handling the module 7.

The supporting block 23 which carries the threaded spindle 22 with yarn lifter 21 at one end and the motor 24 at the other end is screwed to the inside of the front plate 27. The supporting block 23 is so positioned that the yarn lifter 21 projects into the path of movement of the test sample P which is stretched between the thread guide device 6 and the suction nozzle 12 (FIG. 1).

The supporting block 18 for the threaded spindle 17 is situated at a lower level than the supporting block 23 and is screwed to the base plate 29 and the front plate 27 of the module 7. In this embodiment, the threaded spindle 17 is mounted in the supporting block 18 and extends over the whole width of the module 7, as shown in the drawing and the motor 19 is operatively connected to the spindle 17 so as to rotate the spindle. A threaded member such as a nut engages the threaded spindle 17 and is connected to the supporting block 16 with measuring comb 8 situated above the supporting block 18 for the threaded spindle 17 so that when the spindle rotates, the supporting block 16 and with it the measuring comb 8 move in the directionof the axis of the threaded spindle 17. The various electric leads 30 to the measuring comb 8 and to the motors 19 and 24 and the switchs T1 to T6 extend to the rear wall of the Module 7. A ventilator 31 for cooling and ventilating the interior of the module 7 is also mounted on the rear wall of the module.

Although in the example illustrated both the measuring comb 8 and the yarn lifter 21 are driven by means of a motor and a threaded spindle, hydraulic or pneumatic drive means may, of Still other modifications and variations will suggest themselves to persons skilled in the art. It is intended therefore that the foregoing detailed description be understood as exemplary and that the scope of the invention be determined with reference to the following claims.

What is claimed is:

1. Apparatus for testing textile material such as yarns, rovings and slivers, comprising a measuring unit containing a guide device, a measuring instrument, a feed device, and a draw-off device for the test material, the measuring instrument of which unit is formed by a detector component with plate like projections defining gaps of different widths through which the test material is passed during testing, wherein the detector component is displaceable transversely to the direction of movement of the test material and each measuring gap is adjustable to a particular nominal position.

2. Apparatus according to claim 1, wherein the said nominal position is defined by the position of the test material streched between the guide device and the draw off device.

3. Apparatus according to claim 1, including an adjustment device for causing the displacement of said detector component.

4. Apparatus according to claim 3, wherein a detection device is provided for the path of displacement of the dector component.

5. Apparatus according to claim 4, wherein a number of discrete adjustment positions corresponding to the number of measuring gaps is provided for the detector component.

6. Apparatus according to claim 5, wherein the detection device is formed by a number of switches arranged along the path of displacement, corresponding to the number of discrete adjustment positions, wherein the apparatus additionally includes an actuating deivce for these switches.

7. Apparatus according to claim 6, wherein the displacement device is formed by a threaded spindle which engages with a motor driven threaded nut member and which in turn is operatively connected to the detector component so that said detector component is moveable with said spindle.

8. Apparatus according to claim 1, wherein a device for moving the test material out of its measuring gap is provided in the region of the aforsaid nominal position.

9. Apparatus according to claim 8, wherein the detector component and the said device for moving the test material out of its measuring gap are arranged in a common housing which forms a modular unit of the measuring unit and wherein the detector component and the said device for moving the test material out of its measuring gap project from the front of said housing.

10. Apparatus according to claim 9, wherein the test material passes vertically through the given measuring gap and wherein the device for moving the test material out of its measuring gap is arranged upstream of the detector component in the direction of movement of the test material.

11. Apparatus for testing textile material such as yarns, rovings and slivers, comprising a measuring unit containing a guide device, a measuring instrument formed by a detector component with measuring gaps of different widths, a feed unit, a draw off unit for the test material, and a device arranged in the region of the detector component for temporarily removing the test material from its measuring gap and subsequently guiding it back into the gap to provide an interval during which said measuring gaps are free of test material.

12. Apparatus according to claim 11, wherein said detector component is displaceable transversely to the direction of movement of the test material, each measuring gap being adjustable to a particular nominal position, and wherein said device is arranged in the region of this nominal position.

13. Apparatus according to claim 12, wherein said device is formed by an element which has a back and forth movement extending transversely to the test material and by a finger attached to said element.

14. Apparatus according to claim 13, wherein the path of displacement of said element is limited by two end positions, in one of which the test material is completely moved out of the measuring gap while in the other the test material is guided in the measuring gap and is out of engagement with the finger.

15. Apparatus according to claim 14, wherein two switches controlling the drive for the element are associated with the two end positions of the path of displacement of the element and wherein a member movable with said element actuates these switches.

16. Apparatus according to claim 15, wherein said element is a spindle and wherein said finger is fixed to one end of said spindle and extends transversely to the test material and parallel to the direction of displacement of the detector component.

17. Apparatus according to claim 16, wherein said spindle has a threaded portion which engages with a motor driven threaded element.

18. Apparatus according to claim 16, wherein the dector component and the spindle with the finger are arranged in a common housing forms a modular type element of the measuring unit and wherein the detector component and that end of the spindle which carries the finger project from the front plate of said housing.

19. Apparatus according to claim 18, wherein the test material passes through its measuring gap in the vertical direction and wherein spindle with said finger thereon is arranged upstream of the dector component, viewed in the direction of movement of the test material.

20. Apparatus according to claim 19, wherein said spindle with said finger thereon is arranged above the detector component.

* * * * *